APPLE TREE
Filed Sept. 5, 1968 2 Sheets-Sheet 1
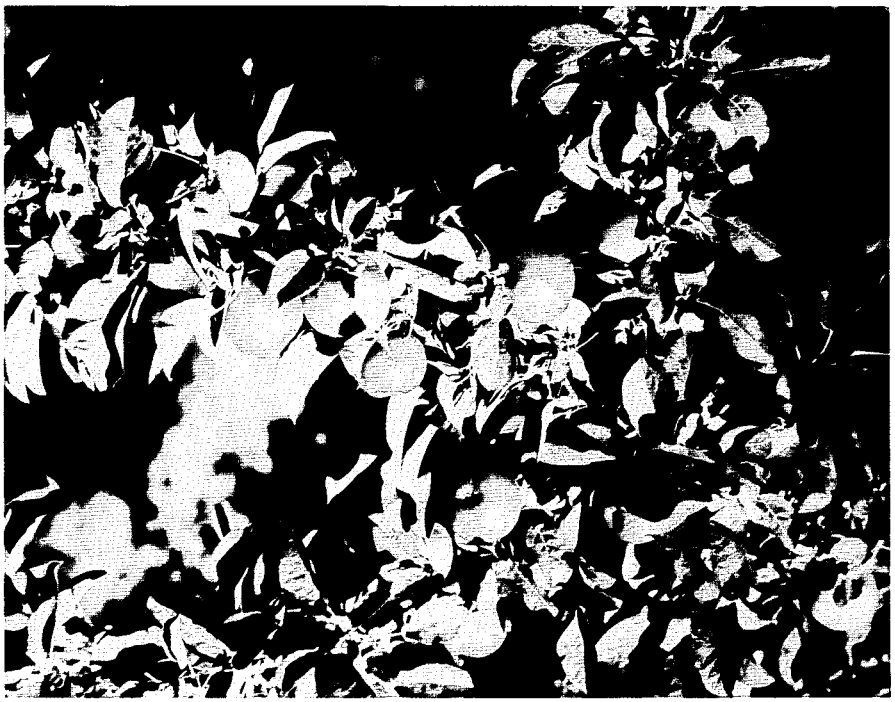
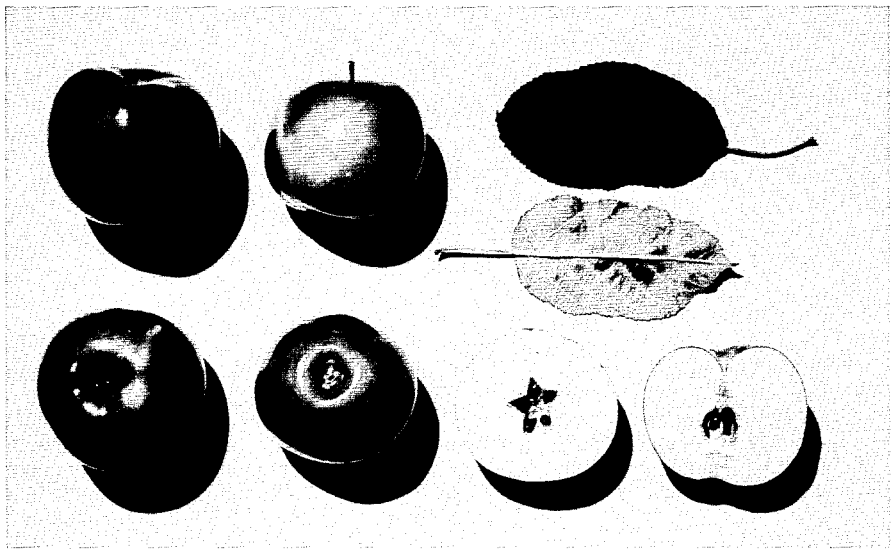
Inventor.
Mervyn Greenslade
By: Robb & Robb
Attorneys.

APPLE TREE
Filed Sept. 5, 1968 2 Sheets-Sheet 2
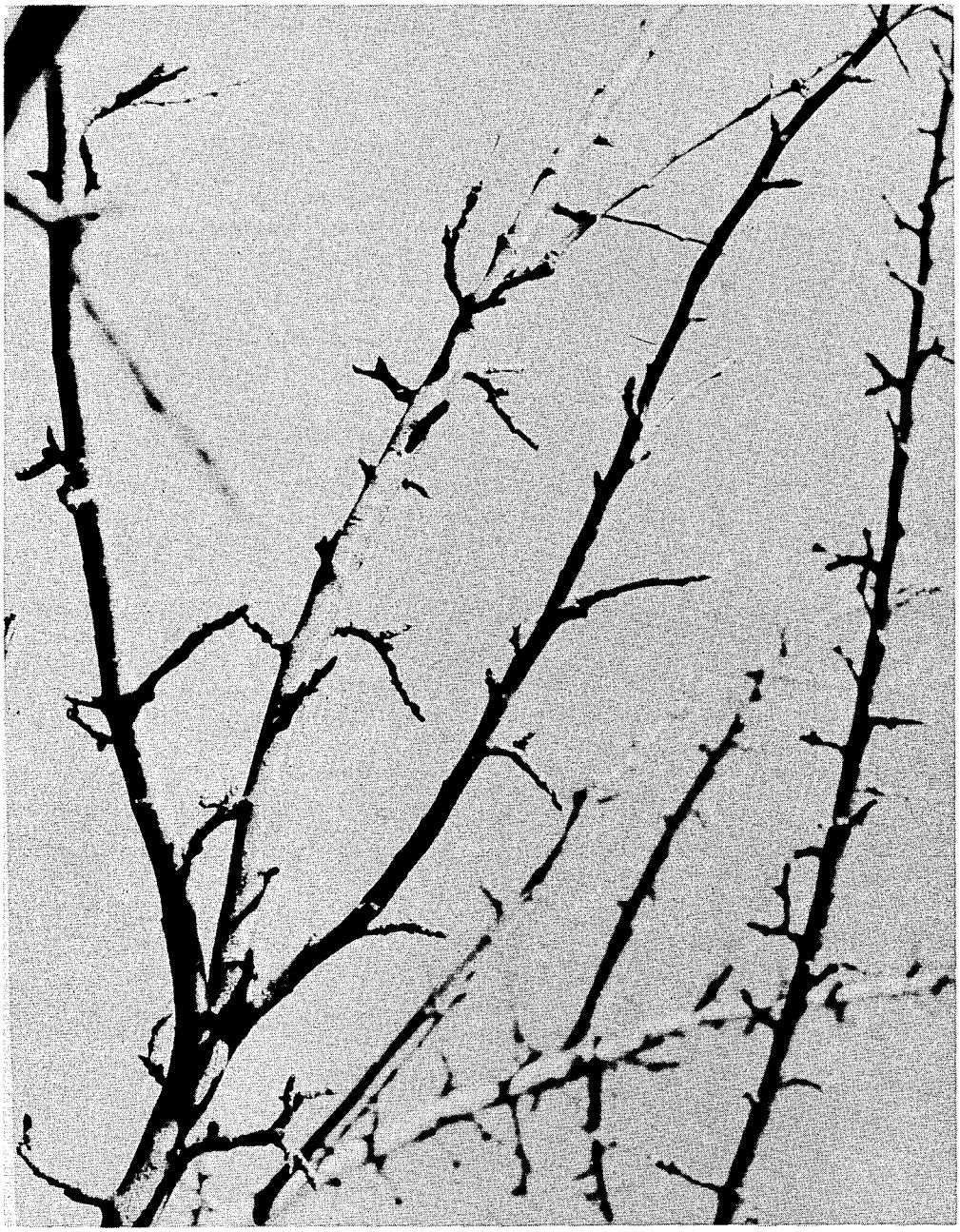
Inventor
Mervyn Greenslade
By: Robbs & Robb
Attorneys.

United States Patent Office

Plant Pat. 2,982
Patented July 28, 1970

2,982
APPLE TREE

Mervyn Greenslade, Summerland, British Columbia, Canada, assignor to Hill Top Orchards and Nurseries, Inc., Hartford, Mich., a corporation of Michigan

Filed Sept. 5, 1968, Ser. No. 757,804
Int. Cl. A01h *5/03*
U.S. Cl. Plt.—34 1 Claim

The present invention relates to a new and distinct variety of apple tree which was discovered by me as a whole tree sport on my cultivated property located at Summerland, in the Province of British Columbia, Dominion of Canada.

At the time of my discovery aforementioned, I was growing apple trees of the variety known as "Summerland Red Mac" (unpatented). In the course of the development and care of these trees, my attention was attracted to one particular tree among the regular plantings which was especially outstanding and which appeared to be materially different in a number of respects from the regular trees of "Summerland Red Mac" growing adjacent thereto under the same conditions. Continued observations and tests of this particular tree, as well as progeny thereof asexually reproduced therefrom by cuttings and by grafting, as performed by me and others on my behalf and under my control, both in British Columbia, Canada and at Hartford, Mich., U.S.A., have convinced me that my new variety originated as a whole tree sport (not a seedling or a hybrid) of "Summerland Red Mac," and is definitely distinguished therefrom and from all other apple varieties of which I am aware, as evidenced by the following unique combination of characteristics which are outstanding therein and which are established and come true through succeeding asexual propagations:

(1) A vigorous and more upright tree habit than that of the variety "Summerland Red Mac," with only a slightly spreading tendency, thereby resulting in a better ability to sustain heavy fruit loads without damaging the tree;

(2) Large, darker green leaves;

(3) A consistently heavy, annular fruit bearing habit;

(4) A habit of bearing the fruit on shorter and heavier fruiting spurs which are more closely spaced and more numerous than those of "Summerland Red Mac" which tend to grow on into secondary vegetative branches and are less numerous and consequently less productive;

(5) A more intense red color of the fruit, while the fruit otherwise being similar to the fruit of "Summerland Red Mac";

(6) A superior resistance to apple powder mildew, while otherwise having disease and insect resistance comparable to "Summerland Red Mac"; and (7) Superior adaptability to growing on many different rootstocks which can be grown under a wide range of cultural conditions and situations.

The accompanying drawing shows typical specimens of the foliage and fruit of my new variety of apple tree as depicted in color as nearly true as it is reasonably possible to make the same in a color illustration of this character, certain of the fruit specimens being shown in both elevation and in plan to disclose the exterior details thereof, and other fruit specimens being shown in both longitudinal and transverse cross-section to disclose the interior details, said drawing also showing in black-and-white a portion of a typical specimen tree in the dormant stage illustrative of its typical spur growth and upright habit.

The following is a detailed description of my new variety, with color terminology in accordance with the Nickerson Color Fan, except where general color terms of ordinary dictionary significance are obvious:

Locality where grown and observed: Summerland, B.C., Canada.

Dates of first and last pickings: Same as "Summerland Red Mac."

Tree: Large; vigorous; upright, with only a slight tendency to spreading; tall; vase-formed; rapid growing; hardy; very productive; regular bearer.

*Trunk.*—Stocky; smooth.

*Branches.*—Thick; smooth; much-branched. Color—gray.

*Lenticels.*—Medium number; medium size.

*Leaves.*—Medium large; medium length (about 3 7/16 inches); wide (about 2 7/16 inches; oval-ovate; abruptly pointed; thick; rugose. Color—dark green. Upper surface—near Dark Yellowish Green Hue 10GY 4/5; under surface—near Moderate Yellow Green, Hue 7.5GY 5/7. Margin—coarsely serrate. Petiole—medium length (about 1 3/8 inches); medium thickness.

Flowers: Early (same as those of "Summerland Red Mac"); large. Color—white.

Fruit:

*Size.*—Mostly uniform, but some variable. Axial diameter—about 2 9/16 inches. Transverse diameter—about 3 inches.

*Form.*—Uniform; symmetrical; regular; slightly compressed laterally; oblate.

*Cavity.*—Symmetrical; flaring toward apex; acuminate evenly; undulate. Depth—about 9/16 inch. Markings—none.

*Basin.*—Unsymmetrical; rounded; flaring; narrow base; undulate; pubescent.

*Stem.*—Medium caliper; pubescent. Length—about 5/8 inch. Bracts present; 1 or 2 in number.

*Calyx.*—Closed; segments persistent; narrowly lanceolate; acute; about 3/16 inch long; separated; ascending; converged from base toward center; both outer and inner surfaces pubescent.

*Eye.*—Partially closed.

*Skin.*—Thin; tough; smooth; glossy; waxed. Dots—obscure; many; small; even; submerged; oblong-circular; color—light green; distribution—uneven. Ground color—greenish yellow. Color markings—blushed; bright; color—similar to "Summerland Red Mac," but more intense red color, with color usually as good or better than the parent fruit. General color effect—near, but somewhat darker than Dark Red, Hue 2.5R 3/7. Bloom—abundant. Scarfskin—wanting.

*Flesh.*—Juicy. Color—white, with greenish yellow tint. Texture—tender; fine. Flavor—subacid; mild; delicate. Aroma—distant. Quality—good.

*Core.*—Median. Bundle area—medium size; broadly oblate; unsymmetrical at base; opposite with cell. Halves of core—unequal. Bundles—inconspicuous; in one whorl; color—yellowish. Alternate bundle—approximate to distant; reaches tube at stamens. Core lines—meeting; indistinct in cross section. Carpellary area—distinct; large. Calyx tube—glabrous toward base; broadly obconic; funnel stem—short; depth of tube to shoulder—about 5/16 inch; entire depth—about 9/16 inch. Styles—present; united; pubescent; glabrous toward apex at point of branching. Stamens—in two obscure whorls; median. Axillary cavity—wanting. Seed cells—open. Cell walls—distant; thick; tough; length—about 3/4 inch; breadth—about 7/16 inch. Longitudinal section—broadly oval; obtuse at apex. Surface—entire; smooth. Cross section—broad.

Seeds: 6 or 7 perfect; from 1 to 4 imperfect; not more than 3 per cell.

*Length.*—About 5/16 inch.

*Breadth.*—About 3/16 inch.

*Form.*—Variable from acute to obtuse.

*Color.*—Light brown.

Use: Local; dessert; culinary.

Keeping quality: Good; storage life the same as "Summerland Red Mac."

Disease and insect resistance; similar to "Summerland Red Mac," but better resistance to apple powdery mildew, as determined by visual observation and by actual counts of infected shoots of the new variety in comparison with neighboring trees of the parent variety and other varieties growing in the same orchard under the same conditions at Summerland, B.C., Canada.

I claim:

1. A new and distinct variety of apple tree, substantially as herein shown and described, characterized particularly as to novelty by the unique combination of a vigorous and more upright tree habit than that of the variety "Summerland Red Mac," with only a slightly spreading tendency, thereby resulting in a better ability to sustain heavy fruit loads without damaging the tree, large, darker green leaves, a consistency heavy, annual fruit bearing habit, a habit of bearing the fruit on shorter and heavier fruiting spurs which are more closely spaced and more numerous than those of "Summerland Red Mac" which tend to grow on into secondary vegetative branches and are less numerous and consequently less productive, a more intense red color of the fruit, while the fruit otherwise being similar to the fruit of "Summerland Red Mac," a superior resistancce to apple powdery mildew, while otherwise having disease and insect resistance comparable to "Summerland Red Mac," and superior adaptability to growing on many different rootstocks which can be grown under a wide range of cultural condiitons and situations.

No references cited.

ROBERT E. BAGWILL, Primary Examiner